US008529757B2

(12) United States Patent
Go et al.

(10) Patent No.: US 8,529,757 B2
(45) Date of Patent: Sep. 10, 2013

(54) PAREX UNIT FEED

(75) Inventors: Anthony Go, Houston, TX (US); Dana Lynn Pilliod, League City, TX (US); John R. Porter, Friendswood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 346 days.

(21) Appl. No.: 12/774,319

(22) Filed: May 5, 2010

(65) Prior Publication Data

US 2010/0305381 A1    Dec. 2, 2010

Related U.S. Application Data

(60) Provisional application No. 61/182,481, filed on May 29, 2009.

(51) Int. Cl.
*B01D 15/10*  (2006.01)
*C07C 7/13*   (2006.01)

(52) U.S. Cl.
USPC ........ 210/198.2; 210/656; 210/659; 585/826; 585/828

(58) Field of Classification Search
USPC ....... 210/656, 659, 198.2; 585/820, 825–827
See application file for complete search history.

(56) References Cited

U.S. PATENT DOCUMENTS

| | | | |
|---|---|---|---|
| 3,040,777 A | 6/1962 | Carson et al. | |
| 3,201,491 A | 8/1965 | Stine et al. | |
| 3,422,848 A | 1/1969 | Liebman et al. | |
| 3,706,812 A | 12/1972 | Derosset et al. | |
| 3,761,533 A | 9/1973 | Otani et al. | |
| 4,006,197 A * | 2/1977 | Bieser | 585/825 |
| 4,029,717 A | 6/1977 | Healy et al. | |
| 4,031,156 A | 6/1977 | Geissler et al. | |
| 4,992,618 A * | 2/1991 | Kulprathipanja | 585/820 |
| 5,750,820 A | 5/1998 | Wei | |
| 5,884,777 A | 3/1999 | Pan et al. | |
| 6,017,448 A | 1/2000 | Hotier et al. | |
| 7,396,973 B1 | 7/2008 | Winter | |
| 2008/0121586 A1 | 5/2008 | Hotier et al. | |
| 2009/0105515 A1 | 4/2009 | Winter et al. | |
| 2010/0125163 A1 | 5/2010 | Porter et al. | |
| 2010/0125613 A1 | 5/2010 | Wiljanen et al. | |

FOREIGN PATENT DOCUMENTS

KR    10-2007-0067922    6/2007

* cited by examiner

*Primary Examiner* — Jennifer A Leung
(74) *Attorney, Agent, or Firm* — Andrew B. Griffis

(57) ABSTRACT

A process for separating a product from a multicomponent feedstream to an adsorption apparatus or system. The apparatus or system may comprise a moving-bed or a simulated moving-bed adsorption means. The product comprises at least one organic compound, such as an aryl compound with alkyl substitutes. In embodiments the conduits used to supply the feedstream to the apparatus or system are flushed with media of multiple grades. In embodiments the process achieves improvements in one or more of efficiency of adsorption separation, capacity of adsorption apparatus systems, and purity of product attainable by adsorption process.

3 Claims, 1 Drawing Sheet

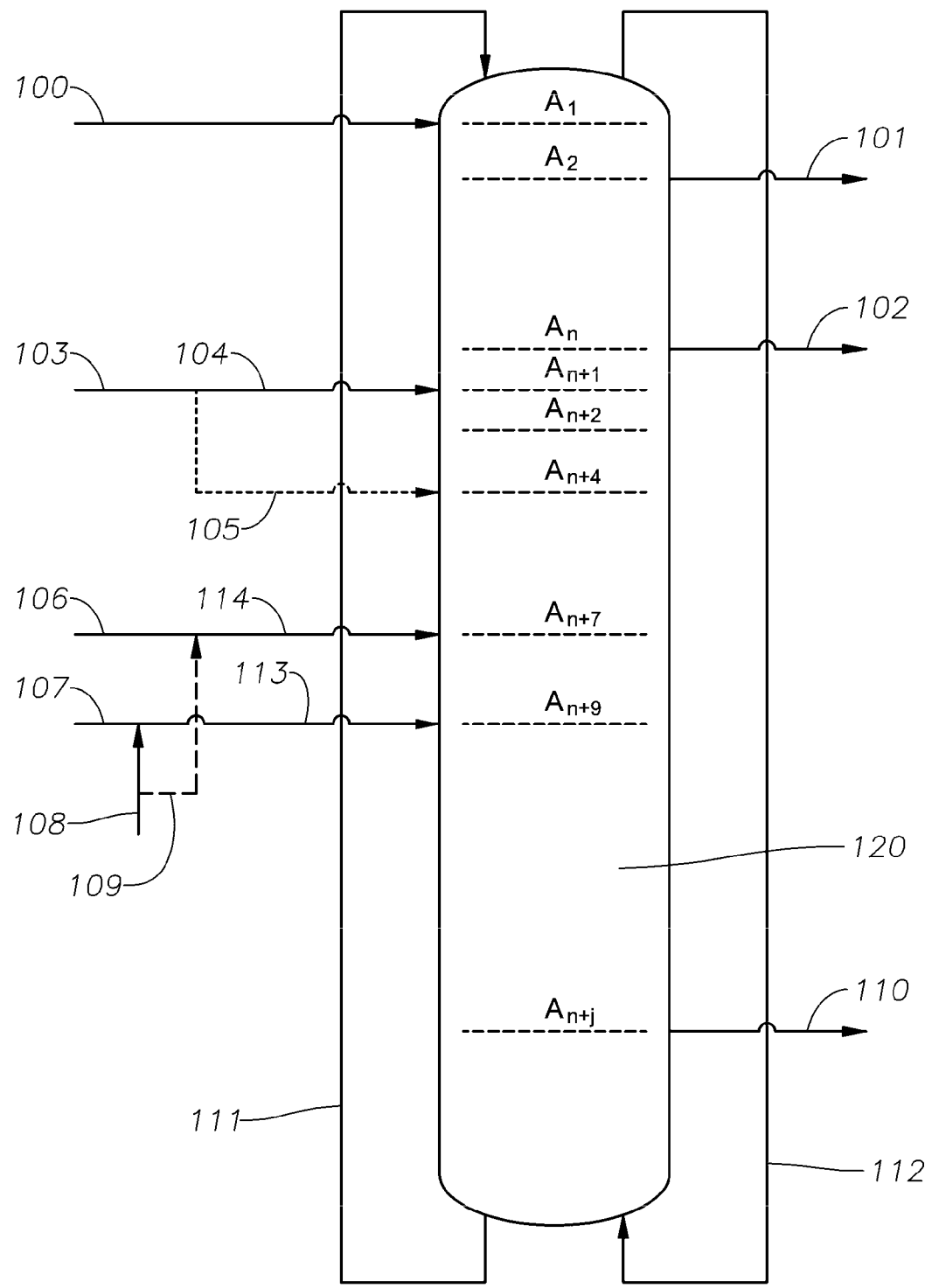

PAREX UNIT FEED

CROSS REFERENCE TO RELATED APPLICATIONS

This application claims the benefit of Provisional Application No. 61/182,481, filed May 29, 2009, the disclosures of which are incorporated by reference in their entireties.

FIELD OF THE INVENTION

The invention relates to a process for separating one or more of the components from two or more multicomponent fluid mixtures, and more particularly to a process for separating organic compounds from such a fluid mixture by means of adsorption apparatus, such as moving-bed or simulated moving-bed adsorption apparatus, or a system comprising such apparatus.

BACKGROUND OF THE INVENTION

Various means are currently available to separate the components of a multicomponent fluid mixture. If the densities of the components differ sufficiently, the effects of gravity over time may be adequate to separate the components. Depending on the quantities of the components involved, a centrifuge may be used to more rapidly separate components with different densities. Alternatively, distillation may be used to separate components with different boiling points.

Some fluid mixtures comprise components which have similar boiling points, and in such cases, separation by distillation may be a difficult and an inefficient means to separate these components. Too many contaminants, e. g., unwanted components, also may evaporate along with (or fail to evaporate from) the desired component(s), or the separation may require high energy expenditures due to the recycling through the distillation process that may be necessary to attain a desired degree of separation or purity.

In view of these and other deficiencies of these aforementioned processes, adsorption often has been preferred as a process for separating the components from a multicomponent fluid mixture to obtain relatively pure products.

The efficiency of an adsorption process may be partially dependent upon the amount of the surface area of the adsorbent solids which is available for contact with a fluid mixture. The surface area available may be more than just the superficial, external surface of the solids. Suitable solids also may have internal spaces. Such internal spaces may comprise pores, channels, or holes in the surface of the solids and may run throughout the solids, much as in sponges. Thus, the fluid contacts not only the superficial surface, but penetrates into the solids. Sieve chambers increase the contact surface between the fluid and the solids in an adsorption process by concentrating them in a confined space. Such structures often are described as molecular sieves, and the volumetric amount of components that may be adsorbed by a molecular sieve is termed the molecular sieve capacity.

In an adsorption process, separation of the fluid components may be accomplished because the material may have a physical attraction for one or more of the components of the mixture in preference to other components of the mixture. Although all of the components of a mixture may be attracted in varying degrees to the material, there is a preference engineered into the process, such that predominantly the desired component(s) may be attracted and remain with the material in preference over all others. Therefore, even if less preferred components of a mixture initially come into contact with a portion of the material, because of the stronger attraction of the material for the desired component(s) of the mixture, the less preferred component(s) may be displaced from the material by the desired, and more strongly preferred, component (s). Although the fluid mixture entering a sieve chamber might be composed of multiple components, the fluid mixture initially leaving the vessel would be composed largely of the components which had been less preferentially adsorbed into the material.

In adsorption processes using adsorbent solids, separation occurs for a period of time, but eventually all the available surface sites on and in the solids are taken up by the desired component(s) or are blocked by concentrations of unwanted components. At that point, little significant additional adsorption of component(s) from the mixture is likely to occur, and the fluid mixture which might be withdrawn from the chamber may be insignificantly changed by further exposure to the solids. The adsorption step of the process is thus ended, and the component(s) which have been adsorbed by the solids must be removed from the solids, so as to effect separation and permit reuse of the solids.

A suitable adsorption apparatus or system might first permit adsorption of a product comprising the desired component(s) by the solids and later treat the solids to cause them to release the product and permit recovery of this product. Such an adsorption apparatus or system might comprise a "moving-bed" which permits movement of a tray or bed of the solids through a chamber, such that at different locations, the solid is subjected to different steps of an adsorption process, e.g., adsorption, purification, and desorption. These steps are defined in greater detail below. Nevertheless, moving the solids through an adsorption apparatus may be difficult and involve complex machinery to move trays or beds. It also may result in loss of the solids by attrition. To avoid these problems, some adsorption apparatus and systems have been designed to "simulate" moving the tray(s) or bed(s) to the locations, e.g., zones, of different steps of an adsorption process. Simulation of the movement of the tray(s) or bed(s) may be accomplished by use of a system of conduits which permits directing and redirecting the streams of fluids into the chamber at different zones at different times. As these stream changes occur, the solids are employed in different steps in an adsorption process as though the solids were moving through the chamber.

The different zones within an adsorption apparatus or system are defined by the particular step of the adsorption process performed within each zone, e.g., (1) an adsorption step in the adsorption zone; (2) a purification step in the purification zone; (3) a desorption step in the desorption zone. A more detailed explanation of the zones of the adsorption process follows.

Adsorption Zone: when a multicomponent fluid feedstream, such as a feedstream comprising the C8 aromatics orthoxylene (OX), metaxylene (MX), paraxylene (PX), and ethylbenzene (EB), is fed into the adsorption apparatus or system, the portion of the apparatus or system into which the feedstream is being fed is termed an "adsorption zone." In the adsorption zone, the fluid comes into contact with the adsorbent material, and the desired component(s) are adsorbed by the adsorbent material. As noted above, other components may also be adsorbed, but preferably to a lesser extent. This preferential adsorption may be achieved by the selection of an adsorbent material, e.g., adsorbent solids, which have a preference for adsorbing the desired component(s) from the multicomponent feedstream. Although only the desired component(s) may have been adsorbed by the solids, other less preferentially adsorbed components of the fluid mixture may still remain in void spaces between the solids and possibly, in the pores, channels, or holes within the solids. These unwanted components preferably are removed from the solids before the desired component(s) are recovered from the solids, so that they are not recovered along with the product.

Purification Zone: after adsorption, the next step is to purify the fluid and adsorbent material in the chamber. In this step, the tray(s) or bed(s) may be moved or flow within the conduits may be changed, so that the multicomponent feedstream may no longer be fed into the adsorption zone. Although the tray(s) or bed(s) have not physically moved, the material may now be described as being in a "purification zone" because a fluid stream, e. g., a purification stream, is fed into the adsorbent material to flush the unwanted components from the adsorbent material, e.g., from within and from the interstitial areas between the solids. Thus, a fluid comprising unwanted components, i.e., raffinate, is flushed from the purification zone by substituting a fluid comprising the desired component(s) or other component(s) deemed to be more acceptable for the unwanted components. The unwanted components may be withdrawn in a raffinate stream. Because an objective of the adsorption process may be to separate the product comprising the desired component(s) from other components which may have nearly the same boiling point or density as the desired component(s), purification may displace, unwanted components and substitute another fluid which can be more readily separated by other means, e.g., distilled.

Desorption Zone. after the solids have been subjected to the purification stream, the stream in the conduit(s) may again be changed to introduce a desorbent steam into the chamber to release the product. The desorbent stream contains desorbent which is more preferentially adsorbed by the solids than the product comprising the desired component(s). The desorbent chosen will depend in part upon the desired component(s), the adsorbent materials, and the ease with which the desorbent can be separated from the product. Once the desorbent stream has been introduced to the chamber, the product may be withdrawn from the chamber.

Each and every step and zone might be present somewhere in an adsorption apparatus or system if simultaneous operations are conducted. Nevertheless, the steps may be performed successively or staggered over time. Further, in some adsorption processes, the unwanted components may be adsorbed, and the product comprising the desired component (s) allowed to pass through the adsorption apparatus or system. Therefore, the terms raffinate and extract are relative and may depend upon the particular nature of the components being separated, the preference of the solids, and the nature of the apparatus or system. Although in embodiments the present invention will be discussed primarily in terms of apparatus and systems in which the product is adsorbed by the solids, the invention is not limited to such configurations.

An apparatus suitable for accomplishing the adsorption process of this invention is a simulated moving-bed adsorption apparatus. A commercial embodiment of a simulated moving-bed adsorption apparatus is used in the well-known Parex Process, which is used to separate C8 aromatic isomers and provide a more highly pure paraxylene (PX) from a less highly pure mixture. See U.S. Pat. Nos. 3,201,491; 3,761, 533; and 4,029,717.

Typically, such an adsorption apparatus is contained in a vertical chamber. Such a chamber may be packed with adsorbent solids, possibly in trays or beds stacked within the chamber. More than one type of solid also might be used. The chamber also may have the capability to perform each of the above-described steps simultaneously within different locations, e.g., zones, in the chamber. Thus, the composition of the fluid in the chamber may vary between zones although there may be no structures completely separating these zones. This may be achieved by the use of a serially and circularly interconnected matrix of fluid communication conduits including associated means, such as valves and pumps, which permit streams to be directed and redirected into different zones of the chamber and to change the direction of these streams through the solids within the different zones of the chamber. The different zones within the chamber may have constantly shifting boundaries, as the process is performed.

The cyclic advancement of the streams through the solids in a simulated moving-bed adsorption apparatus may be accomplished by utilizing a manifold arrangement to cause the fluid to flow in a counter current manner with respect to the solids. The valves in the manifold may be operated in a sequential manner to effect the shifting of the streams in the same direction as overall fluid flow throughout the adsorbent solids. In this regard see U.S. Pat. No. 3,706,812. Another means for producing a countercurrent flow in the solid adsorbent is a rotating disc valve by which the streams, e.g., feed, extract, desorbent, and raffinate, and line flush, are advanced cyclically in the same direction through the adsorbent solids. Both U.S. Pat. Nos. 3,040,777 and 3,422,848 disclose suitable rotary valves. Both suitable manifold arrangements and disc valves are known in the art. More recently, a system has been described using dual rotary valves (U.S. application Ser. No. 61/116097, filed 19 Nov. 2008).

Normally there are at least four streams (feed, desorbent, extract, and raffinate) employed in the procedure. The location at which the feed and desorbent streams enter the chamber and the extract and raffinate streams leave the chamber are simultaneously shift in the same direction at set intervals. Each shift in location of these transfer points delivers or removes liquid from a different bed within the chamber. In many instances, one zone may contain a larger quantity of adsorbent material than other zones. Moreover, zones other than those discussed above may also be present. For example, in some configurations, a buffer zone between the adsorption zone and the desorption zone may be present and contain a small amount of adsorbent material relative to the zones surrounding it. Further, if a desorbent is used that can easily desorb extract from the adsorbent material, only a small amount of the material need be present in the desorption zone in comparison to the other zones. In addition, the adsorbent need not be located in a single chamber, but may be located in multiple chamber or a series of chambers.

Introducing and withdrawing fluids to the beds may comprise a plurality of fluid communication conduits, and the same fluid communication conduit may be used in a first instance to input a feedstream into the apparatus or system and later to withdraw an extract stream. This can result in reduced product purity due to contamination of the withdrawn product. Fluid communication conduits may contain unwanted components, such as residue remaining in the conduit from earlier additions or withdrawals of streams. This problem may be overcome by employing separate conduits for each stream or by removing such residue from the conduits by flushing them with a medium which would not effect product purity as adversely as would a unwanted component remaining in the fluid communication conduit. A preferred flushing medium has been the product or the desorbent, which might be more readily separated downstream of the chamber than would the residue. See U.S. Pat. No. 4,031,156. Nevertheless, flushing conduits with the product reduces the output of the adsorption process.

A standard Parex unit for separating paraxylene (PX) from metaxylene (MX), and orthoxylene (OX) has a single feed to a single rotary valve or parallel rotary valves. The rotary valve directs the feed to a bed line, which is somewhere between the extract (which may comprise, by way of example, 99.7% PX and desorbent) and the raffinate (PX-depleted xylenes and desorbent) withdrawal points. Since the UOP Parex process is a simulated moving bed process, the bed lines are shared with all of the feed and product streams, and therefore the bed lines must be flushed between the feed injection point and the extract withdrawal point in order to prevent contamination of the product.

A standard UOP parex unit has a primary flush which removes the majority of contaminants and a secondary flush which removes trace impurities just before the extract point. Because the standard UOP Parex unit has a single feed, various streams of different compositions are typically blended together and fed to a single point in the Parex process.

However, as indicated in U.S. Pat. No. 5,750,820, and also U.S. Pat. No. 7,396,973, it is better to segregate feeds which are of substantially different composition, such as concentrated paraxylene from a selective toluene disproportionation unit (generally 85-90% paraxylene) and equilibrium xylenes (generally about 23% paraxylene) from a powerformer, isomerization unit or transalkylation unit. This can be done by using the primary line flush as a second feed point for the paraxylene concentrate and using the secondary flush as the sole flushing stream. Having only a single flush does result in a slight compromise in the separation process, but the compromise typically is far outweighed by the benefit of optimizing the feed location of the paraxylene concentrate as far as net purity in the final product.

However, there is a problem with the above configuration in that the standard Parex unit has the secondary flush located close to the extract withdrawal point in order to minimize contaminants that are withdrawn with the extract. When the secondary flush is very close to the extract withdrawal point, the concentrated paraxylene that is being flushed from the bed line will be too close to the extract withdrawal point and the highest separation of the feed will not be realized. This has heretofore not been recognized.

The present inventors have surprisingly discovered that the feed location of both the concentrated paraxylene in the primary flush and also the location of the secondary flush can be modified to realize the full benefit of the feed configuration in U.S. Pat. No. 5,750,820. By moving the secondary flush further away from the extract, the material flushed from the bed line will be injected at a more efficient location. In embodiments, improvements associated with less desorbent recirculation can be realized.

SUMMARY OF THE INVENTION

The invention is directed to a process for separating a product from at least two multicomponent feeds to an apparatus or system for the continuous simulated countercurrent adsorptive separation of hydrocarbons, and to the apparatus or system for accomplishing the same.

In embodiments, the process comprises feeding at least two different feeds, the feeds characterized by having different concentrations of at least one product, preferably a C8 species selected from one or more isomers of xylene, or the feeds may be characterized as having a different desired product, for instance paraxylene as the desired product of a first feed and orthoxylene as the desired product of a second feed. It will be recognized by one of skill in the art that a continuous simulated countercurrent adsorptive separation system can have many desired end products, such as pharmaceuticals, fragrances, sugars, and the like.

In embodiments, the feed location of both the primary flush and also the secondary flush are altered as compared with the prior art to realize the fullest benefit of the present invention.

In embodiments the conduits used to supply the feedstream to the apparatus or system are flushed with media of multiple grades.

In embodiments, the process achieves improvements in one or more of efficiency of adsorption separation, capacity of adsorption apparatus systems, and purity of product attainable by adsorption process.

In one embodiment, the process comprises the steps of: (a) introducing a first multicomponent feed, comprising at least one desired product, through at least one fluid communication conduit into a simulated moving-bed adsorption apparatus comprising at least one rotary valve and plural sieve chambers; (b) flushing the at least one conduit in step (a) with a sufficient quantity of at least one initial flushing medium comprising the at least one desired product in step (a) in an initial concentration, such that feed residue is flushed from the at least one conduit in step (a) into the apparatus by the at least one initial medium; (c) flushing the at least one conduit in step (a) with a sufficient quantity of a second and preferably final flushing medium, wherein said second flushing medium is selected from the group consisting of desorbent, such as paradiethylbenzene (PDEB), toluene, or a mixture thereof, and a flushing medium comprising the at least one desired product in step (a) in a final concentration, such that the final concentration is not less than and is optionally greater than the initial concentration and such that initial medium residue from the at least one initial medium is flushed from the conduit in step (a) into the apparatus by the final medium; (d) withdrawing the at least one desired product in step (a) from the apparatus; (e) introducing a second multicomponent feed comprising at least one desired product, which may be the same or different from the at least one desired product in step (a) and which, if the same, is present in the second multicomponent feed in a concentration different from the concentration of the at least one desired product in said first multicomponent feed, through at least one fluid communication conduit into the apparatus; (f) flushing the at least one conduit in step (d) with a sufficient quantity of at least one initial flushing medium (which may be the same or different from the flushing medium in step (b)) comprising the at least one desired product in step (e) in an initial concentration, such that feed residue is flushed from the at least one conduit in step (e) into the apparatus by the at least one initial medium in step (f); (g) withdrawing the at least one desired product in step (d) from the apparatus.

In embodiments, the quantity of the initial medium may not be less than that sufficient to flush the feedstream residue from the conduit.

In embodiments, the apparatus comprises plural sieve chambers containing one or more adsorbent material selected from the group consisting of charcoal, ion-exchange resins, silica gel, and the like, and the quantity of the initial medium may be sufficient to fill the apparatus to the sieve chamber capacity.

In embodiments, the process includes additional steps including one or more of flushing one or more conduits with a sufficient quantity of a final (or third) flushing medium comprising the at least one desired component in a final concentration, such that the final concentration is greater than the initial concentration and greater than the second concentration, and such that initial medium residue from the at least one initial medium is flushed from the conduit into the system by the final medium; withdrawing a raffinate stream from the system; introducing a desorbent stream to the system; withdrawing a combination comprised of the product and the desorbent from the system; and removing the product from the combination.

In yet another embodiment, the initial concentration of the at least one initial medium is continuously increased during the flushing of the at least one conduit until the initial concentration equals the final concentration. Preferably, this may be accomplished by adding the product to the at least one initial medium in gradually increasing amounts and decreasing proportionately flow from the source of the at least one initial medium.

As is well-known per se in the commercial Parex unit, moving the locations of liquid input and output is accomplished by a fluid directing device known generally as a rotary valve which works in conjunction with distributors located between the adsorbent sub-beds. The rotary valve accomplishes moving the input and output locations through first directing the liquid introduction or withdrawal lines to specific distributors located between the adsorbent sub-beds. After a specified time period, called the step time, the rotary valve advances one index and redirects the liquid inputs and outputs to the distributors immediately adjacent and downstream of the previously used distributors. Each advancement of the rotary valve to a new valve position is generally called a valve step, and the completion of all the valve steps is called a valve cycle. The step time is uniform for each valve step in a valve cycle, and is generally from about 60 to about 90 seconds. A typical process contains 24 adsorbent sub-beds, 24 distributors located between the 24 adsorbent sub-beds, two liquid input lines, two liquid output lines, and associated flush lines. In an embodiment of the present invention, an improvement is provided whereby the rotary valve is replumb so that the input of the secondary flush is a least one and preferably two valve steps downstream of where it is, heretofore, ordinary inputted. This is more fully illustrated by the description of FIG. 1 below. This also means that the secondary flush is added closer in sequence to the input of the primary flush, such as within three cycle steps.

It is an object of the invention, in one or more embodiments, to increase the efficiency of adsorption apparatus or systems, whereby contaminants, such as feedstream residue, may be removed from fluid communication conduits by flushing them from the conduits into the apparatus or system with flushing media containing concentrations of the desired component(s) of the product which are higher than that of the feedstream. It is an advantage of such embodiments that if the product is extracted through the same conduits that carried the feedstream, such as in a simulated moving-bed adsorption apparatus, extract will not be contaminated, or will have lower contamination, with feedstream residue.

It is an additional object of this invention to increase the capacity of an adsorption apparatus or system. It is an advantage of this process that excess capacity of the apparatus or system may be more fully utilized by purifying the solids with flushing media and flushing conduits with media containing the desired component(s). It is a feature of such embodiments that fluid communication conduits may be flushed with media containing concentrations of a desired component or components higher than that of the feedstream, which may be drawn from a source other than the apparatus.

It is yet another object of this invention, in embodiments, to increase the purity of the product obtained from an adsorption apparatus or system. It is a feature of embodiments of this process that contaminants may be removed from conduits and from pores, channels, and holes in adsorbent solids, and conduits may be charged with the product. It is an advantage such embodiments that the product may be recycled through the apparatus or system, and excess apparatus or system capacity may be used to further separate other unwanted components of the feedstream remaining in the product.

These and other objects, features, and advantages will become apparent as reference is made to the following detailed description, preferred embodiments, examples, and appended claims.

BRIEF DESCRIPTION OF THE DRAWINGS

In the accompanying drawing, like reference numerals are used to denote like parts throughout the several views.

FIG. 1 is a schematic illustrating a comparison of the prior art with an embodiment of the invention.

DETAILED DESCRIPTION

According to the invention, there is provided a process for separating a product from at least two multicomponent feeds to an adsorption apparatus or system. The apparatus or system may comprise a moving-bed or a simulated moving-bed adsorption means, and in embodiments provides a product comprising at least one organic compound, such as an aryl compound with alkyl substitutes. In embodiments the conduits used to supply the feedstream to the apparatus or system are flushed with media of multiple grades. In embodiments the process achieves improvements in one or more of efficiency of adsorption separation, capacity of adsorption apparatus systems, and purity of product attainable by adsorption process.

In embodiments the feed location of both the concentrated paraxylene in the primary flush and also the location of the secondary flush are located to realize the full benefit of feed locations. In embodiments, by moving the secondary flush further away from the extract, the material flushed from the bed line will be injected into a more advantageous point in the profile. This allows for additional capacity or decreased use of energy associated with a decrease of desorbent recirculation will be realized.

The process of an embodiment of the present invention employs the simulated countercurrent flow processes such as described in U.S. Pat. Nos. 3,201,491; 3,761,533; and 4,029,717. The diagram in FIG. 1 will be understood by those of skill in the art to depict a simulated moving bed process. Desorbent is introduced through conduit 100, flush leaves the apparatus through conduit 101, extract (containing the desired product) leaves the apparatus via conduit 102, raffinate leaves the system through conduit 110, the secondary flush is added through conduit 103, the primary flush is added through conduit 106, a first multicomponent feed is added to the system through conduit 107 and a second multicomponent feed is added through lines 108 or 109, as explained more fully in the following description.

In FIG. 1, the adsorbent 112 moves upward through the sieve chamber vessel 120 containing plural bedlines A1 through An+j. The hydrocarbon liquid feed 111 flows countercurrent to the circulating adsorbent. In operation, the adsorbent does not flow, but the various feed and product streams cycle through the bed lines, represented by lines $A_1$ through $A_{n+j}$, at a rate that is different than the circulating hydrocarbon. This simulates the movement of the bed lines $A_1$ through $A_{n+j}$. Theoretically there may be any number of bed lines, thus n>2 and n+j is the maximum number of bedlines, however from a practical standpoint the number of bed lines is limited by design considerations and other factors. A further discussion may be found in the prior art. What is important is the relative positions of the bedlines caused by the stepping of the rotary valve, as would be understood by one of skill in the art (such as that n and j are positive integers and that in typical commercial embodiments the total number of bedlines is 24). Certain bedlines, i.e., bedlines between $A_2$ and $A_n$, bedlines $A_{n+3}$, $A_{n+5}$, $A_{n+6}$, and $A_{n+10}$ through $A_{n+j-1}$ are not depicted in FIG. 1, for convenience of view.

In a conventional unit, the sieve preferentially starts adsorbing the paraxylene molecules in the feed 107 and flows upward. In embodiments, the feed is selected from the group consisting of equilibrium xylenes and ethylbenzene (which is about 21-24 wt % PX), concentrated PX from an STDP unit (which is about 85-90 wt %), and admixtures thereof.

The paraxylene is desorbed from the sieves in the bedlines by desorbent stream 100, the main component of which also is strongly adsorbed on the sieve(s) in bedlines $A_1$ through $A_{n+j}$, but has a different boiling point and is easily separated from the desired product(s) downstream of the apparatus. In embodiments, the desorbent is paradiethylbenzene (PDEB), toluene, or a mixture thereof, or some other strongly adsorbed compound.

The extract 102, which in the embodiment described is a mixture of the purified paraxylene and the desorbent, is withdrawn at a point between the feed 107 and the desorbent 100. The raffinate 110, which consist of the paraxylene-depleted (less strongly adsorbed) xylenes and desorbent.

Because this is a simulated moving bed process, the various feeds and products must share the lines between the bedlines (sieve beds) and rotary valve (not shown). To prevent loss of paraxylene molecules in the hydrocarbon recycle 111 and subsequently the raffinate 110, the bed lines between the extract out 102 and desorbent in 100 are flushed 101. The flush out can either be sent to the extract tower for recovery or recycled and used for primary flush in 106.

In addition (and more importantly), since feed 113 is routed through the transfer lines (not shown) between the rotary valve (also not shown) and the sieve chambers $A_1$ through $A_{n+j}$ before extract 102 the transfer line should be thoroughly flushed to avoid contamination of the product extract 102. Either finished paraxylene product or desorbent, e.g., PDEB or toluene, are routed through a primary flush 114 and a secondary flush 104. The secondary flushing step is just after the extract withdrawal location 102 in order to flush any trace amounts of contaminants that may have leaked from the sieve chamber(s) back into the bed lines.

As taught in U.S. Pat. No. 5,750,820, it is an improvement to segregate concentrated paraxylene, such as may be obtained downstream from 102 by distillation and then recycle, and use it as primary flush 114 in place of location 106. This step is beneficial because it routes the concentrated paraxylene into a more optimum place in the composition profile. In addition, while the concentrated paraxylene 109 is not as pure as desorbent 100 or product paraxylene (extract 102 is a combination of product para-xylene and desorbent, which can be separated downstream such as by distillation), it does reduce the amount of contaminants in the bed lines $A_1$ through $A_{n+j}$ and facilitate the secondary flushing step.

However, flushing a bed line (i.e., $A_1$ through $A_{n+j}$) full of concentrated PX (85-90 wt %) right next to the extract creates a problem which was unanticipated and not even recognized by the inventors of the aforementioned improvement. Without wishing to be bound by theory, what happens is that you are now flushing in a material that has about 10 vol % impurities when you are trying to get down to 2-3 wt % impurities.

The present inventors, having discovered the problem, have now also discovered that in order to realize the full benefit of the movement of the input of the concentrated stream in line 108 from 107 to 106 via line 109, the feed location of the secondary flush 103 must be moved to an improved place in the composition profile, e.g., further from 104, and closer to 113. One embodiment of such is depicted in FIG. 1 as line 105. Again, it should be emphasized, as would be known by one of skill in the art, that these positions are relative and that, although the actual positions change by virtue of the movement of the rotary valve (not shown), the relative positions of the lines remains the same.

It will be understood by one of ordinary skill in the art that FIG. 1 depicts a simplified simulated moving-bed apparatus with a rotary valve, wherein countercurrent "movement" of the solids in bed lines $A_1$ through $A_{n+j}$ relative to the fluid streams is simulated by the use of the rotary valve, which is not shown in the figure. As the valve rotates, the zones previously discussed move through the column in a stepwise sequence due to the change in the stream flows through the valve. In embodiments, a preferred rotary valve for performing this invention is described in U.S. Pat. No. 3,205,166, the disclosure of which is incorporated herein by reference. In this arrangement, each fluid communication conduit connected to the chamber may serve a different function with each step rotation of the rotary valve.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

What is claimed is:

1. An apparatus for the continuous simulated countercurrent adsorptive separation of hydrocarbons comprising plural sieve chambers fluidly connected with plural bedlines A1 through An+j, wherein n>2 and n+j is the total number of bedlines, which in turn are fluidly connected with a matrix of fluid communication conduits to distribute plural input streams, including desorbent, a primary flush input and a secondary flush input, and at least two multicomponent feeds differing in the concentration of paraxylene, to said plural bedlines, and plural output streams, including a primary flush output and a secondary flush output, an extract comprising a paraxylene-enriched product, and raffinate, from said plural sieve chambers, the improvement comprising: when bedline An contains extract, bedline An+9 contains a first multicomponent feed, bedline An+7 contains a second multicomponent feed, then said secondary flush input is contained in a bedline between bedlines An+2 and bedline An+7.

2. The apparatus of claim 1, wherein the first multicomponent feed has a concentration of paraxylene of at least about 23 wt % and the second multicomponent feed has a concentration of paraxylene above about 80 wt %.

3. The apparatus of claim 1, wherein the secondary flush comprises about 100 wt % paradiethylbenzene.

* * * * *